United States Patent [19]
Hoffman et al.

[11] Patent Number: 6,071,272
[45] Date of Patent: Jun. 6, 2000

[54] METHOD FOR TREATING ERECTILE DYSFUNCTIONALITY

[76] Inventors: Alan S. Hoffman, 4426 Sarong, Houston, Tex. 77096; Benjamin Tripp, 22179 Primrose Way, Boca Raton, Fla. 33433

[21] Appl. No.: 08/959,161

[22] Filed: Oct. 28, 1997

[51] Int. Cl.[7] .................................................. A61M 31/00
[52] U.S. Cl. ............................... 604/500; 604/68; 604/70
[58] Field of Search ................................ 604/49, 68, 70, 604/71, 72, 131–137, 155, 140–141

[56] References Cited

U.S. PATENT DOCUMENTS

| | | | |
|---|---|---|---|
| 4,941,880 | 7/1990 | Burns | 604/143 |
| 5,439,938 | 8/1995 | Synder et al. | 514/565 |
| 5,474,535 | 12/1995 | Place et al. | |
| 5,503,627 | 4/1996 | McKinnnon et al. | 604/72 |
| 5,520,639 | 5/1996 | Peterson et al. | |
| 5,569,189 | 10/1996 | Parsons | |
| 5,599,302 | 2/1997 | Lilley et al. | 604/68 |
| 5,741,511 | 4/1998 | Lee et al. | 424/449 |
| 5,836,911 | 11/1998 | Marzynski et al. | 604/72 |

OTHER PUBLICATIONS

Morales et al., "Oral and topical treatment of erectile dysfunction present and future". Urologic Clinics of North America, Nov. 1995, 22(4): 880–886.

Fallon, Intracvernous Injection Therapy for male Erectile Dysfunction?, Urologic Clinics of North America, Nov. 1995, 22(4):833–845.

Baum et al., "A Practical Approach to the Evaluation and Treatment of Erectile Dysfunction. A Private Practitioner's Viewpoint", *Urologic Clinics of North America*, Nov. 1995, 22(4): 865–877.

Coscelli et al., "Safety, efficacy, acceptability of a pre–filled insulin pen in diabetic patients over 60 years old", *Diabetes Research and Clinical Practice*, 1995, 28:173–177.

Chen et al., "Penile Scarring with Intracavernous Injection Therapy Using Prostaglandin El: A Risk Factor Analysis", *The Journal of Urology*, Jan. 1996, 155:138–140.

Chandru et al., "Long–Term Follow–Up of Patients Receiving Injection Therapy for Erectile Dysfunction", *Urology*, 1997, 49(6):932–935.

deMeyer et al., "Influence of the Method of Intracavernous Injection on Penile Rigidity: A Possible Pharmacokinetic Explanation", *Urology*, 1997, 49(2): 248–252.

Fallon, "Intracavernous Injection Therapy for Male Erectile Dysfunction", *Urologic Clinics of North America*, Nov. 1995, 22(4): 833–845.

Ginsberg, "The Role of Technology in Diabetes Therapy", *Diabetes Care*, Jun. 1994, 17 Supplement 1: 50–55.

Gupta et al., "Predictors of Success and Risk Factors for Attrition in the Use of Intracavernous Injection", *The Journal of Urology*, May 1997, 157:1681–1686.

Gheorghiu et al., "Quality of life in Patients Using Self–Administered Intracavernous Injections of Prostaglandin E1 for Erectile Dysfunction", *The Journal of Urology*, Jul. 1996, 156:80–81.

ICN Pharmaceuticals, Inc. Advertisement: Patients appreciate the choice, TESTRED C–III Methyltestosterone capsules, USP, 10 mg, 1 page.

Hornquist et al., "Change in quality of life along with type 1 diabetes", *Diabetes Research and Clinical Practice*, 1995, 28:63–72.

(List continued on next page.)

*Primary Examiner*—Wynn Wood Coggins
*Assistant Examiner*—Kevin C. Sirmons
*Attorney, Agent, or Firm*—Duane, Morris & Heckscher LLP

[57] ABSTRACT

This invention relates to a method for treating erectile dysfunctionality by injecting pharmacological agents into the corpora cavernosa of the penis. The present invention employs an improved method for injecting pharmacological agents into the corpora cavernosa of the penis which does not require a hypodermic needle and the attendant problems associated with the use of hypodermic needles to inject pharmacological agents into the penis and to provide a new treatment option to many patients with erectile dysfunctionality.

22 Claims, 2 Drawing Sheets

OTHER PUBLICATIONS

Helltrom et al., A Double–Blind, Placebo–Controlled Evaluation of the Erectile Response to Transurethral Alprostadil, *Urology*, 1996, 48(6):851–852.

"Proceedings of the American Urological Association", *The Journal of Urology*, May 1996, 155(5):469A, 470A, 676A.

Jarrow et al., "Outcome Analysis of Goal Directed Therapy of Impotence", *The Journal of Urology*, May 1996, 155(5):1609–1612.

Kim et al., "Advances in the Treatment of Organic Erectile Dysfunction", *Hospital Practice*, Apr. 1997, 101–120.

Limoge et al., "Minimally Invasive Therapies in the Treatment of Erectile Dysfunction in Anticoagulated Cases: A Study of Satisfaction and Safety", *The Journal of Urology*, Apr. 1996, 155:1277–1279.

Morales et al., "Oral and topical treatment of erectile dysfunction Present and future", *Urologic Clinics of North America*, Nov. 1995, 22(4): 880–886.

Mulcahy, "Editorial: Impotence", *The Journal of Urology*, Apr. 1996, 155:1280.

Paper Nos. 697–712, *The Journal of Urology*, 157(4)Supplement, 180–183.

Padma–Nathan et al., "Treatment of Men with Erectile Dysfunction with Transurethral Alprostadil", *The New England Journal of Medicine*, Jan. 1996, 336(1)1–7.

Rosen et al., "The International Index of Erectile Function (IIEF): A Multidimensional Scale for Assessment of Erectile Dysfunction", *Urology*, 1997, 49(6):822–830.

Willke et al., "Quality of Life Effects of Alprostadil Therapy for Erectile Dysfunction", *The Journal of Urology*, Jun. 1997, 157:2124–2131.

Seyam, et al., "Evaluation of a No–Needle Penile Injector: A Preliminary Study Evaluating Tissue Penetration and its Hemodynamic Consequences in the Rat", *Urology*, 1997, 50(6), 994–998.

METHOD FOR TREATING ERECTILE DYSFUNCTIONALITY

BACKGROUND OF THE INVENTION

1. Field of the Invention

This invention relates to a method for treating erectile dysfunctionality by injecting pharmacological agents into the corpora cavemosa of the penis. The present invention employs an improved method for injecting pharmacological agents into the corpora cavernosa of the penis which does not require a hypodermic needle and the attendant problems associated with the use of hypodermic needles to inject pharmacological agents into the penis and to provide a new treatment option to many patients with erectile dysfunctionality.

2. Description of the Prior Art

There are a variety of methods for the treatment of erectile disfunctionality. These methods include vacuum/constriction devices, cutaneous placement of pharmacological ointment, pharmacological injection using a hypodermic needle, penile prostheses, vascular surgery, and urethral implantation of pharmacological agents. (See Kim et at, "Advances In the Treatment of Organic Erectile Dysfunction", *Hospital Practice*, Apr. 15, 1997). The present invention is directed towards an improved method of delivering pharmacological agents to the penis for the treatment of erectile dysfunctionality.

The direct injection of pharmacological agents by a needle into the penis has many drawbacks. First, many patients have an aversion to Injecting their penis with a hypodermic needle. Other side effects of intracavernous injection include pain, hematoma, priapism, and fibrotic complications, including penile nodules, curvature and fibrotic plaques (See Helistrom, "A Double-Blind Placebo-Controlled Evaluation Response of the Erectile Response To Transurethral Alprostadil" *Urology*, (1996). Additionally, needle injection involves a risk of accidentally puncturing a nerve or blood vessel (See "Biojector® 2000 Product Information and Benefits of the Biojector® 2000 Needle-Free Injection Management System", by Biolet, Inc.). Long term patent compliance with needle injection of the penis is less than 50% (see Hellstrom, supra).

Another prior art method of delivering pharmacological agents to the penis is intraurethral insertion of a suppository. The primary pharmacological agent delivered by this method is alprostadil. The drawbacks of this method include the cost, estimated to be $20–25 per application, pain, and the efficacy. Studies have shown that the transurethral suppository method of treatment has an efficacy of less than 50%, even where the dosage of alprostadil is 1000 micrograms (See Kim, supra).

Mechanical methods of inducing a penile erection include vacuum/constriction devices. Such devices are clumsy and cumbersome. The cumbersome nature of these devices interferes with user spontaneity. Another drawback of this treatment method is a lack of erectile rigidity proximal to the constriction band of such devices. This results in the swinging of the penis about the constriction band, in a manner similar to the movement of a pendulum. Such movement is referred to as a "hinge" effect.

Two methods of treating erectile dysfunctionality which require surgery are the implantation of a penile prosthesis and vascular surgery. Surgery is expensive and may not be suitable for all patients. Additionally, the implantation of a penile prosthesis precludes subsequent use of vasoactive injection therapy and vacuum/constriction devices. Vascular surgery is presently considered investigational and should only be performed in a research setting (Kim, supra).

A third treatment comprising cutaneous placement of a pharmacological ointment, has low response rates (Kim, supra).

The present invention provides an improved method of treating erectile dysfunctonality. In particular, the present invention provides an improved method for delivering pharmacological agents to the corpora cavemosa of the penis. The advantages of the present invention over prior art methods for delivering pharmacological-agents to the corpora cavernosa of the penis include less pain, greater speed, less blood loss, less invasion, less tissue damage and less risk of transmitting blood borne diseases and viruses than methods involving the use of a hypodermic needle. The present invention does not require the use of a hypodermic needle in order to deliver pharmacological agents to the corpora cavernosa of the penis. Infection can result from the use of a needle that is improperly sterilized. Accordingly, the invention does not involve the needle disposal or Infection problems of methods which use hypodermic needles. Additionally, there is no risk of a stick injury from the use of a used needle.

The present invention provides several psychological advantages over intravenous injection methods. These advantages include no needle anxiety, no painful injections and improved sexual spontaneity.

The present invention provides several physical advantages over intracavernous injection. These advantages include less penile trauma, less hematoma, less penile induration, less plaque, less penile fibrosis, less penile deformation, less penile shortening, and less blood vessel injury.

The present invention does not require surgery. It is therefore far less expensive than methods of treating erectile dysfunctionality which require surgery.

The only device required to use the present invention is a hand held injection unit for injecting pharmacological agents into the side of the penis, without the use of a hypodermic needle. This hand held device is smaller and less cumbersome than vacuum/constriction devices.

SUMMARY OF THE INVENTION

The present invention is directed towards a method for treating erectile dysfunctionality with a pharmacological agent The method of the present invention is an improved method for delivering a pharmacological agent to the corpora cavernosa of the penis.

The present invention comprises grasping the head region of the penis and stretching the penis such that it is in tension. A needleless injector containing a pharmacological agent suitable for the treatment of erectile dysfunctionality Is placed against the side of the penis. The pharmacological agent is then injected into the corpora cavemosa of the penis without any needle penetration of the penis.

The Biojector® 2000 by Biojet, Inc. is a suitable needleless injector for use in practicing the present invention. The term "needleless injector", as used herein, refers to any device capable of injecting a pharmacological agent into the body without penetrating the body with a needle.

Needleless injectors include injectors comprising a fluid driven injection device and/or a spring driven injection device, wherein fluid pressure and/or spring force are used to impart sufficient velocity to a fluid pharmacological agent to inject it into the body without the use of a needle. Needleless injectors may also be electrically driven.

Needleless injectors are disclosed in U.S. Pat. No. 5,520,639 to Peterson et al; U.S. Pat. No. 5, 569,189 to Parsons; and U.S. Pat. No. 5, 599,302 to Lilley et al. The disclosures of the three aforementioned U.S. Patents are expressly incorporated herein by reference.

For the purposes of the present invention, the needleless injector must be capable of imparting sufficient velocity to the pharmacological agent to inject it through the fascia of the penis and into the corpora cavernosa of the penis. In a preferred embodiment, the needleless injection is capable of injecting 1.0 cc of pharmacological agent solution into the corpora cavernosa of the penis. Although the actual depth of penetration required to reach the corpora cave mosa will vary as a function of the circumferential dimensions of the penis, in a preferred embodiment the needleless Injector should be capable of injecting a pharmacological agent to a depth of at least 5 millimeters Into a side of the penis.

The pharmacological agents which are suitable for the treatment of erectile dysfunctionality and which may be employed with the present invention include, but are not limited to, vasodilators such as prostagiandin E1 or E0, phosphodiesterase inhibitors, nitric oxide donors or precursors such as L-arginine, potassium channel activators, alpha-adrenergic antagonists such as phentolamine, calcium channel blockers, antidepressants, smooth muscle relaxants such as papaverine, atropine, and Maxi-K+ channel openers or gene products.

DESCRIPTION OF THE PREFERRED EMBODIMENTS

Figure 1:
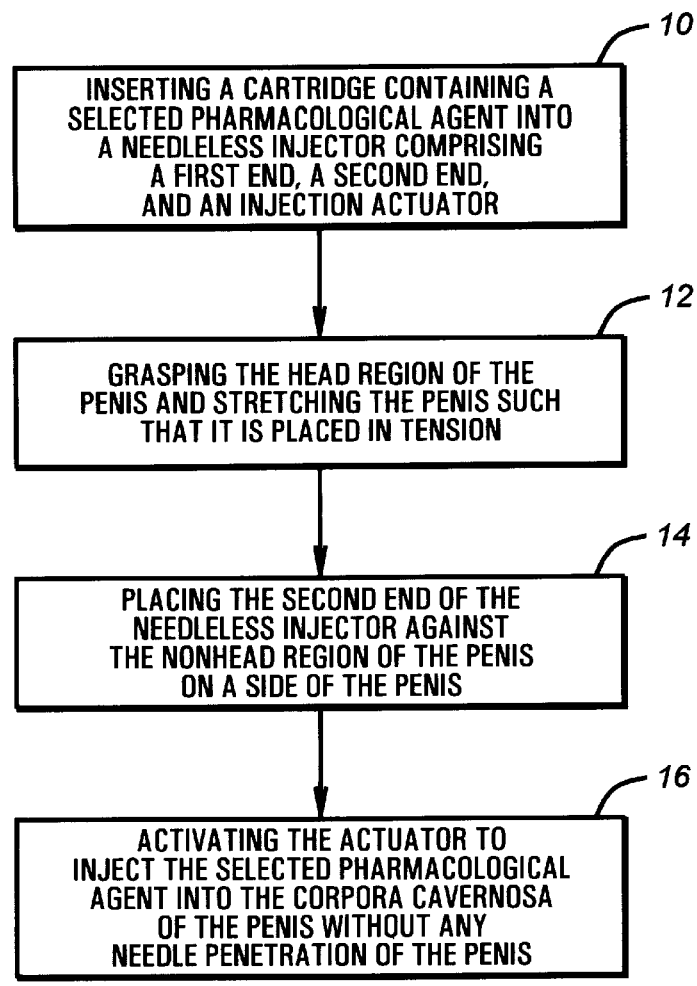
FIG. 1 is a block diagram of a first method embodiment of the present invention.
Figure 4A:
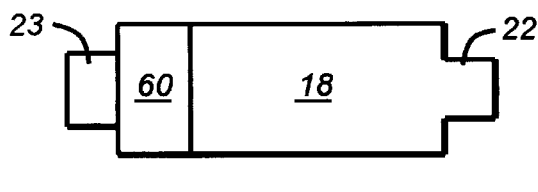
FIGS. 4a–4b are side cross sectional views of needleless injectors suitable for use with the present invention.
Figure 4B:
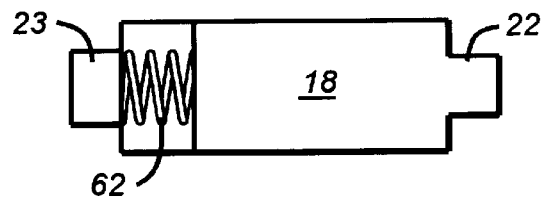
Figure 3:
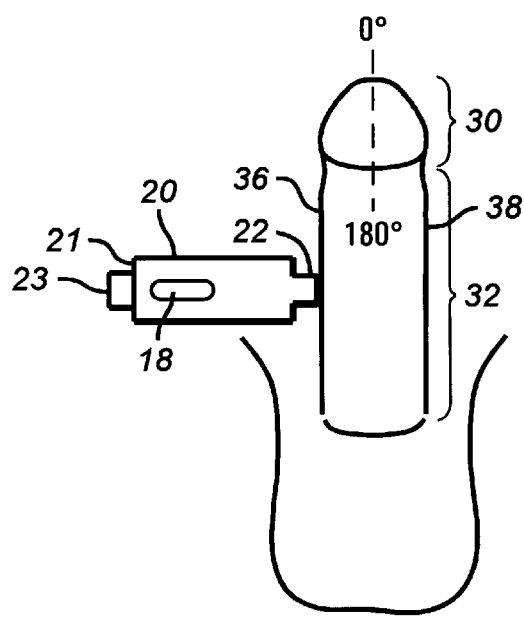
FIG. 3 is a front view of the method of the present invention being used to deliver pharmacological agents to a penis.

The present invention comprises inserting a volume 18 of selected pharmacological agent into a needleless injector device 20 comprising a first end 21, a second end 22, and an injection actuator 23, as shown in block 10 of FIG. 1 and FIG. 3. In a preferred embodiment, the volume may be a cartridge. In other preferred embodiments, the needleless injector may comprise a fluid driven injection device 60 or a spring driven injection device 62, as shown in FIGS. 4a–4b. In a preferred embodiment, the injection device does not contain a needle. In a preferred embodiment, the injection device is a Biojector® 2000 injector, available from Biojet, Inc.

Figure 2:
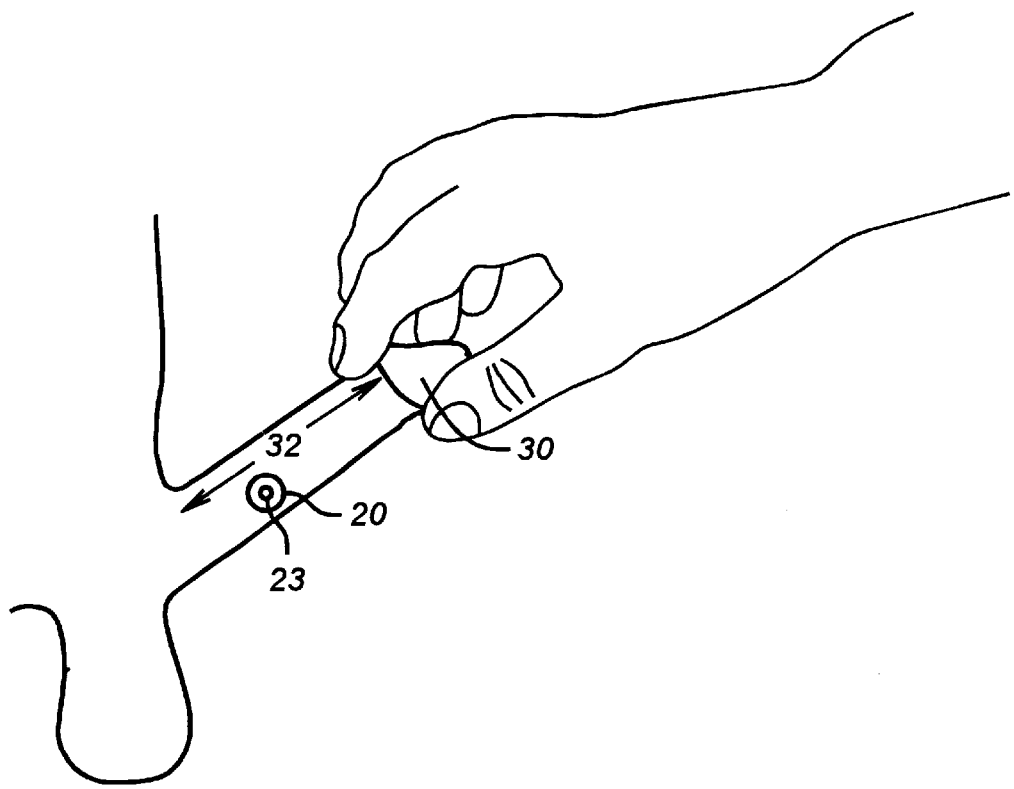
FIG. 2 is a side view of the method of the present invention being used to deliver pharmacological agents to a penis.

The invention further comprises grasping the head region of the penis 30 and stretching the penis such that it is placed in tension, as shown in block 12 of FIG. 1 and in FIG. 2. In a preferred embodiment, the penis is stretched at an angle of. 30 to 150 degrees relative to the upper body of the patient. In a preferred embodiment, the side of the penis against which the injector is placed encompasses a region within the azimuthal angles of 60 to 120 degrees and 240 to 300 degrees, where 0 degrees is the top of the penis and 180 degrees is the bottom of the penis, as shown in FIG. 3. In a preferred embodiment, the injection is not placed at the 0° or 180° positions of the penis.

The second end of the injection device is placed against the nonhead region of the penis 32 on aside of the penis 36 or 38, as shown in block 14 of FIG. 1 and in FIGS. 2 and 3. The term "nonhead region", as used herein, refers to any region of the penis, other than the head region. The actuator is activated to cause the needleless injector to inject the selected pharmacological agent into the corpora cavernosa of the penis without any needle penetration of the penis, as shown in block 16 of FIG. 1.

In a preferred embodiment, the actuator causes pressurized fluid to inject the pharmacological agent into the corpora cavemosa of the penis. In a preferred embodiment, the actuator is a button as shown in FIG. 3. In this embodiment, the actuator may be activated by depressing the button.

The foregoing disclosure and description of the invention are illustrative and explanatory thereof, and various changes in the size, shape and materials, as well as in the details of the illustrated construction, may be made without departing from the spirit of the invention.

What is claimed is:

1. A method for delivering a pharmacological agent into a person's penis, comprising a head region, a nonhead region and a corpora cavernosa, said method comprising:

a. inserting a volume of selected pharmacological agent into a needleless injector comprising a first end, a second end, and an injection actuator;

b. grasping the head region of the penis and stretching the penis such that it is placed in tension;

c. placing the second end of the needleless injector against the nonhead region of the penis on a side of the penis; and d. activating the actuator to inject the selected pharmacological agent into the corpora cavernosa of the penis without any needle penetration of the penis.

2. The method of claim 1, wherein said needleless injector comprises a fluid driven injection device.

3. The method of claim 1, wherein said needleless injector comprises a spring driven injection device.

4. The method of claim 1, wherein said selected pharmacological agent comprises a component selected from the group consisting of phosphodiesterase inhibitor or a vasodilator.

5. The method of claim 1, wherein said selected pharmacological agent comprises a component selected from the group consisting of nitric oxide donor or precursor.

6. The method of claim 1, wherein said selected pharmacological agent comprises a potassium channel activator.

7. The method of claim 1, wherein said selected pharmacological agent comprises an alpha-adrenergic antagonist.

8. The method of claim 1, wherein said selected pharmacological agent comprises a calcium channel blocker.

9. The method of claim 1, wherein said actuator comprises a button.

10. The method of claim 9, wherein said activating is accomplished by depressing the button.

11. The method of claim 1, wherein the person comprises an upper body and the penis is stretched at an angle of 30 to 150 degrees relative to the upper body of the person.

12. A method for inducing a penile erection, in a penis comprising a head region, a nonhead region and a corpora cavernosa, said method comprising:

a. inserting a volume of selected pharmacological agent suitable for the treatment of erectile dysfunctionality into a fluid driven needleless injector device comprising a first end, a second end, and an injection actuator;

b. grasping the head region of the penis and stretching the penis such that it is placed in tension;

c. placing the second end of the injector device against the nonhead region of the penis on a side of the penis; and d. activating the actuator to cause pressurized fluid to inject the selected pharmacological agent into the corpora cavernosa of the penis without any needle penetration of the penis.

13. The method of claim 12, wherein said selected pharmacological agent comprises a vasodilator.

14. The method of claim 12, wherein said selected pharmacological agent comprises an antidepressant.

15. The method of claim 12, wherein said selected pharmacological agent comprises a nitric oxide donor.

16. The method of claim 12, wherein said selected pharmacological agent comprises a component selected from the group consisting of potassium channel activator or smooth muscle relaxant.

17. The method of claim 12, wherein said selected pharmacological agent comprises atropine.

18. The method of claim 12, wherein said selected pharmacological agent comprises a Maxi-$K^+$ channel opener or gene product.

19. A method for treating erectile dysfunctionality with a pharmacological agent, in a penis comprising a head region, a nonhead region and a corpora cavernosa, said method comprising:

a. grasping the head region of the penis;

b. stretching the penis such that it is in tension;

c. placing a needleless injector containing a selected pharmacological agent suitable for the treatment of erectile dysfunctionality against a side of the penis, in the nonhead region of the penis; and d. injecting the pharmacological agent into the corpora cavernosa of the penis without any needle penetration of the penis.

20. The method of claim 19 wherein said selected pharmacological agent comprises component selected from the group consisting of prostaglandin E1 or E0.

21. The method of claim 19 wherein said selected pharmacological agent comprises L-arginine.

22. The method of claim 19 wherein said selected pharmacological agent comprises component selected from the group consisting of phentolamine or papaverine.

* * * * *